(12) United States Patent
Yoo et al.

(10) Patent No.: US 10,987,397 B2
(45) Date of Patent: Apr. 27, 2021

(54) CATECHIN-FREE TEA WATER AND COMPOSITION CONTAINING SAME

(71) Applicant: AMOREPACIFIC CORPORATION, Seoul (KR)

(72) Inventors: Se Jin Yoo, Yongin-si (KR); Seon Su Han, Yongin-si (KR); Hyang Tae Choi, Yongin-si (KR); Song Seok Shin, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 170 days.

(21) Appl. No.: 15/121,874

(22) PCT Filed: Feb. 27, 2015

(86) PCT No.: PCT/KR2015/001934
§ 371 (c)(1),
(2) Date: Aug. 26, 2016

(87) PCT Pub. No.: WO2015/130131
PCT Pub. Date: Sep. 3, 2015

(65) Prior Publication Data
US 2017/0007535 A1    Jan. 12, 2017

(30) Foreign Application Priority Data

Feb. 28, 2014 (KR) ........................ 10-2014-0024064

(51) Int. Cl.
| | |
|---|---|
| *A61K 36/00* | (2006.01) |
| *A61K 36/82* | (2006.01) |
| *A61K 8/9789* | (2017.01) |
| *A61Q 19/00* | (2006.01) |

(52) U.S. Cl.
CPC ............ *A61K 36/82* (2013.01); *A61K 8/9789* (2017.08); *A61Q 19/00* (2013.01); *A61Q 19/007* (2013.01); *A61K 2800/74* (2013.01)

(58) Field of Classification Search
CPC ..................................................... A61K 36/00
USPC ....................................................... 424/725
See application file for complete search history.

(56) References Cited

U.S. PATENT DOCUMENTS

| | | |
|---|---|---|
| 9,089,504 B2 | 7/2015 | Kang et al. |
| 2007/0178175 A1 | 8/2007 | Matsubara et al. |
| 2010/0068363 A1 | 3/2010 | Unno et al. |
| 2012/0251635 A1 | 10/2012 | Rha et al. |
| 2014/0186315 A1 | 7/2014 | Kang et al. |

FOREIGN PATENT DOCUMENTS

| | | | |
|---|---|---|---|
| CN | 1921869 A | | 2/2007 |
| CN | 102711527 A | | 10/2012 |
| EP | 1741343 | * | 1/2007 |
| JP | 3623247 B2 | | 2/2005 |
| KR | 10-2007-0003936 A | | 1/2007 |
| KR | 10-2013-0010984 A | | 1/2013 |
| KR | 10-2013-0022471 A | | 3/2013 |
| WO | 97/30597 A1 | | 8/1997 |
| WO | 2013/027984 A2 | | 2/2013 |

OTHER PUBLICATIONS

Leung et al., American Society for Nutritional Sciences, 2248-2251, 2001.*
International Search Report and English Translation from International Patent Application No. PCT/KR2015/001934, dated Apr. 30, 2015.
Written Opinion from International Patent Application No. PCT/KR2015/001934, dated Apr. 30, 2015.
Office Action from Chinese Patent Application No. 201580023572.4 (dated Aug. 1, 2018).

* cited by examiner

*Primary Examiner* — Michael V Meller
(74) *Attorney, Agent, or Firm* — Merchant & Gould P.C.

(57) ABSTRACT

When a catechin-free tea water according to the present invention is contained in a cosmetic or pharmaceutical composition, enzymes are inactivated and catechin contained in tea leaves is removed by steaming unprocessed raw tea leaves, thereby preventing the oxidation of tea water. Therefore, a composition containing the tea water according to the present invention can prevent offensive odor generation or discoloration of the composition, thereby enabling the stable use thereof in various industrial fields such as food, cosmetics and medicine. In addition, plenty of skin helpful ingredients, contained in raw tea leaves, can be contained, and thus excellent skin barrier function recovery or skin moisturization effects can be provided.

12 Claims, 8 Drawing Sheets

*: Stastical significancy exists,(p<0.05 by Independent samplest-test)
†: Stastical significancy exists,(p<0.05 by Mann-Whitney U test)
※: TEWL change(g/m² h) = TEWL value of Visit N − TEWL value of Visit2

CATECHIN-FREE TEA WATER AND COMPOSITION CONTAINING SAME

CROSS-REFERENCE TO RELATED APPLICATIONS

This application is a National Stage Application of International Patent Application No. PCT/KR2015/001934, filed 27 Feb. 2015, which claims benefit of Serial No. 10-2014-0024064, filed 28 Feb. 2014 in the Republic of Korea and which applications are incorporated herein by reference. To the extent appropriate, a claim of priority is made to each of the above disclosed applications.

TECHNICAL FIELD

The present disclosure relates to a catechin-free tea water, a composition containing the same and a method for preparing the catechin-free tea water.

BACKGROUND ART

Tea water is prepared by brewing the bud or leaf of Camellia sinensis in the family Theaceae. It has been used as a drink from before Christ. Beneficial pharmacological mechanisms of active ingredients contained in tea water, such as catechins, amino acids, vitamin C, β-carotene, dietary fibers, etc., are being elucidated gradually. In particular, the effects of the ingredients contained in tea including antioxidant, antiaging, anticancer, blood cholesterol-lowering, heavy metal-detoxifying, anticavity and bad breath-preventing effects, are drawing a lot of attentions.

Among them, the tea catechins have antioxidant, anticancer, cardiovascular disease-preventing and detoxifying effects because they can bind easily to various substances due to many hydroxyl (—OH) groups. Therefore, a method for preparing tea water rich in catechins among the useful ingredients of green tea is being studied actively.

However, catechin worsens the preference for tea as a drink due to its astringent taste. In addition, due to the presence of many hydroxyl (—OH) groups, browning of tea occurs due to oxidation when the tea is stored at room temperature. Moreover, the catechin often interrupts the uptake of other active ingredients contained in the tea such as caffeine.

Accordingly, when a cosmetic or a medicine is prepared using a catechin-containing tea water, there are problems in that other active ingredients contained in the tea water are oxidized, thereby lowering their efficacy and causing offensive odor generation and discoloration.

REFERENCES OF RELATED ART

Korean Patent Publication No. 2013-0010984.
Korean Patent Publication No. 2013-0022471.

DISCLOSURE

Technical Problem

The present disclosure is directed to providing a catechin-free tea water for use as a cosmetic or a medicine, a composition containing the same and a method for preparing the tea water.

Technical Solution

In an aspect, the present disclosure provides a catechin-free tea water containing 1 wt % or less of catechin based on the total weight of the tea water.

In another aspect, the present disclosure provides a composition for external application to skin and a composition for recovering skin barrier function or moisturizing skin, which contain the catechin-free tea water.

In another aspect, the present disclosure provides a method for preparing the catechin-free tea water, which includes: a step of obtaining a tea juice by steaming raw tea leaf, thereby inactivating enzymes, and juice-extracting the same; and a step of obtaining a catechin-free tea water by removing catechin from the extracted tea juice.

Advantageous Effects

A catechin-free tea water according to the present disclosure is prepared by steaming unprocessed raw tea leaf, thereby inactivating enzymes and preventing oxidation of the tea leaf, and then removing catechin. Therefore, a cosmetic or pharmaceutical composition containing the tea water according to the present disclosure is prevented from offensive odor generation and discoloration and thus can be used stably in various industrial fields such as food, cosmetics, medicine, etc.

In addition, the tea water according to the present disclosure is prevented from offensive odor generation and discoloration by removing catechin. Because the catechin-free tea water according to the present disclosure contains minerals, amino acids and free sugars derived from raw tea leaf in large amounts, it can provide superior effect of recovering skin barrier function or moisturizing skin.

BEST MODE

Figure 1:
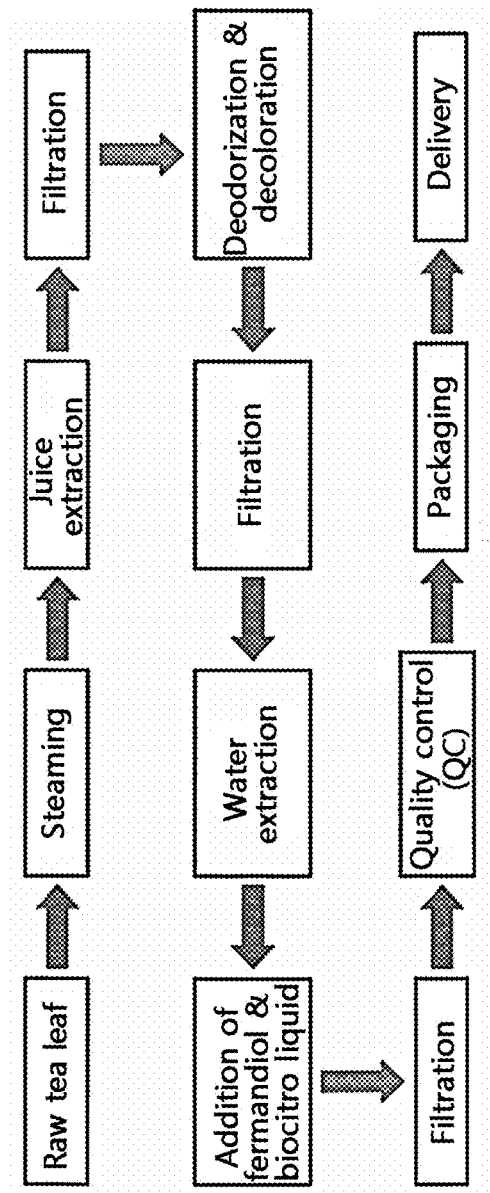
FIG. 1 shows a procedure of preparing a catechin-free tea water according to an exemplary embodiment of the present disclosure and preparing a cosmetic composition containing the same.

Korean Patent Application No. 10-2014-0024064 filed on Feb. 28, 2014 is incorporated herein by reference in its entirety. This application claims the priority of Korean Patent Application No. 10-2014-0024064 which is incorporated herein by reference in its entirety.

In the present disclosure, "skin" refers to the tissue that covers the surface of the body of an animal. The term is used in the broadest concept, including not only the tissue covering the surface of the body and face but also hair and scalp.

In the present disclosure, "tea water" broadly refers to any liquid derived from tea leaf. Specifically, it may be water obtained after steeping unprocessed or processed tea leaf in the water, an extract of tea leaf, a liquid obtained by condensing the vapor that is generated by heating tea leaf, a liquid obtained by steaming tea leaf and then extracting after adding cold water or ionized water, or the like. The tea water contains not only water but also ingredients beneficial to human, contained in tea leaf.

Hereinafter, the present disclosure is described in detail.

The present disclosure provides a catechin-free tea water containing 1 wt % or less of catechin based on the total weight of the tea water. Specifically, the present disclosure may provide a tea water containing 0.5, 0.3, 0.1, 0.01 or 0.0001 wt % or less of catechin. More specifically, the present disclosure may provide a tea water containing no catechin at all.

In the present disclosure, "raw tea leaf" refers to unprocessed tea leaf. The "tea leaf" refers to the bud or leaf of Camellia sinensis and is not limited in its quality or kind. Specifically, tea leaf harvested in spring, summer or autumn may be used and okro tea whose chlorophyll content has been increased by shading the light may also be used, although not being limited thereto. Dried tea leaf or processed tea leaf is problematic in that water, volatile ingredients and other water-soluble ingredients contained in the tea leaf are lost during heating. In contrast, because the raw tea leaf used in the present disclosure is rich in minerals and amino acids, it can provide an effect of recovering skin barrier function and moisturizing skin when applied to the skin.

The catechin has a structure of Chemical Formula 1. Specifically, gallocatechin (GC), epigallocatechin (EGC), catechin (C), caffeine (CAF), epicatechin (EC), epigallocatechin gallate (EGCG), gallocatechin gallate (GCG), epicatechin gallate (ECG), catechin gallate (CG), etc. are referred to as tea catechins.

[Chemical Formula 1]

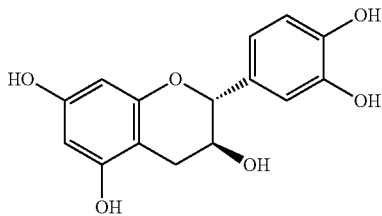

In general, tea leaf contains 10-15% of tea catechins based on its total dry weight and EGCG accounts for 50-60% of the tea catechins. However, it is known that the contents vary depending on climate, soil condition or tea species. As seen from Chemical Formula 1, because the catechin has many hydroxyl (—OH) groups, it exhibits useful effects for human such as antioxidant effect. On the other hand, when the catechin is contained in tea water, it lowers the activities of other active ingredients when the tea water is stored at room temperature due to the hydroxyl groups. In addition, offensive odor generation and discoloration of the tea water occur as the catechin is oxidized. Accordingly, it is difficult to ensure stability when it is used for cosmetics.

The present disclosure provides a tea water derived from raw tea leaf in which enzymes are inactivated, specifically a tea water obtained by steaming raw tea leaf and then removing catechin. For example, it may provide a tea water obtained by steaming raw tea leaf and then removing catechin by adsorbing catechin followed by filtering. In an exemplary embodiment of the present disclosure, the inactivated enzyme may include polyphenol oxidase.

Specifically, a method for preparing the catechin-free tea water according to the present disclosure includes: a step of obtaining a tea juice by steaming raw tea leaf, thereby inactivating enzymes, and juice-extracting the same; and a step of obtaining a catechin-free tea water by removing catechin from the extracted tea juice. The preparation method according to the present disclosure is described in detail referring to FIG. 1.

First, in the step of obtaining the tea juice, a tea juice is obtained after inactivating enzymes of raw tea leaf (raw material). The raw tea leaf may be one that has been stored in a refrigerator to prevent oxidation by oxygen.

Also, in the step of obtaining the tea juice, the enzymes in raw tea leaf may be inactivated by contacting the raw tea leaf with steam (steaming). The steaming may be performed at 90-110° C., specifically 95-105° C., more specifically 97-103° C. And, the steaming may be performed for 0.1-3 minutes, specifically 0.1-2 minutes, more specifically 25-35 seconds. In accordance with the present disclosure, by inactivating enzymes through the steaming treatment, oxidation in tea leaf may be prevented and the yield of tea juice may be increased by softening plant tissue. When the temperature and time of the steam are above the higher limits, thermal oxidation may occur. And, when temperature and time are below the lower limits, the enzymes may not be inactivated 100% and enzymatic oxidation may occur.

In the step of obtaining the tea juice by juice-extracting the raw tea leaf in which the enzymes are inactivated, the juice extraction may be performed by one or more method selected from gear-type juice extraction, press-type juice extraction, grinding-type juice extraction and enzymatic degradation-type juice extraction, specifically by press-type juice extraction.

In an exemplary embodiment of the present disclosure, the process of removing the catechin may include: a deodorization and decoloration step of adsorbing ingredients causing offensive odor generation and discoloration including catechin from the extracted tea juice; and a filtration step of filtering the tea juice that has passed through the deodorization and decoloration step through a filter, thereby removing the adsorbed ingredients causing offensive odor generation and discoloration including catechin and residual solids.

In an exemplary embodiment, the deodorization and decoloration step may include adsorbing the ingredients causing offensive odor generation and discoloration including catechin with one or more of diatomaceous earth and activated carbon. The ingredients causing offensive odor generation and discoloration include colored ingredients such as chlorophyll. Specifically, the method of adsorbing the ingredients causing offensive odor generation and discoloration using diatomaceous earth includes passing the extracted tea juice through diatomaceous earth, and the method of adsorbing the ingredients causing offensive odor generation and discoloration using activated carbon includes adding activated carbon to the extracted tea juice and reacting each other. In another exemplary embodiment of the present disclosure, the deodorization and decoloration step may include removing the ingredients causing offensive odor generation and discoloration including catechin through precipitation using an organic solvent, high-pressure treatment, etc. However, any method capable of removing catechin may be used without limitation.

In an exemplary embodiment, in the filtration step, the adsorbed ingredients causing offensive odor generation and discoloration including catechin and residual solids may be removed by passing the tea juice that has passed through the deodorization and decoloration step through a filter having a pore size of 0.2-1.5 μm, more specifically 1 μm.

In an exemplary embodiment of the present disclosure, the step of obtaining the tea water may further include, after removing catechin from the tea juice, obtaining the tea water by extracting water-soluble ingredients using water, an organic solvent or a mixture thereof. In an exemplary embodiment, the organic solvent may include, for example, a polyol such as 1,3-butylene glycol and 1,3-propylene glycol and its concentration may be, for example, 0.1-12%.

The catechin-free tea water prepared according to the present disclosure may be prevented from the denaturation of other physiologically beneficial ingredients contained in raw tea leaf because of preventing oxidation of the tea water caused by catechin. Accordingly, the tea water is prevented from offensive odor generation and discoloration and the effect of other beneficial ingredients may be exerted effectively.

The present disclosure also provides a composition for external application to skin which contains the catechin-free tea water. In another exemplary embodiment, the present disclosure provides a composition for recovering skin barrier function or moisturizing skin which contains the catechin-free tea water. In an exemplary embodiment, the composition may contain 0.01-100 wt %, specifically 0.015, 0.1, 1, 10, 20, 30, 40, 50 or 60 wt % or more and 100, 90 or 80 wt % or less, of the catechin-free tea water based on the total weight of the composition.

The skin barrier function refers to the function of protecting skin from various stimuli from external environments, such as chemicals, air pollutants, dryness, UV, etc., and preventing excessive water loss from the skin. This function can be maintained only when the stratum corneum (horny layer) composed of keratinocytes is formed normally. Specifically, during keratinization (differentiation of epidermal cells) when old keratinocytes are removed from skin and replaced with new keratinocytes, the keratinocytes form the stratum corneum while producing natural moisturizing factors (NMFs) and intracellular lipids (ceramides, cholesterols, fatty acids, etc.), such that the stratum corneum has firmness and flexibility so as to function as a skin barrier. However, the stratum corneum can readily lose its function due to habitual factors such as excessive face washing, bathing, etc., environmental factors such as dry air, pollutants, etc., and endogenous diseases such as atopic skin, senile skin, etc. The breakdown of the skin barrier function causes various skin diseases such as skin dryness, atopic dermatitis, contact dermatitis, psoriasis, etc.

Because the catechin-free tea water according to the present disclosure is rich in minerals, amino acids, free sugars, etc. derived from raw tea leaf, which promote the differentiation of keratinocytes, and is free of catechin, the tea water can exert its function effectively without being oxidized. Accordingly, a composition containing the same may provide a superior effect of recovering or enhancing skin barrier function and moisturizing skin.

In an exemplary embodiment, the present disclosure may provide a cosmetic composition containing the catechin-free tea water, which is a cosmetic composition for recovering skin barrier function or moisturizing skin.

Specifically, the cosmetic composition according to the present disclosure may contain a cosmetically or dermatologically acceptable medium or base. It may be provided in the form of any topically applicable formulation, for example, a solution, a gel, a solid, an anhydrous paste, an oil-in-water emulsion, a water-in-oil emulsion, a multiemulsion, a suspension, a microemulsion, a microcapsule, a microgranule, an ionic (liposome) or nonionic vesicular dispersion, a cream, a skin lotion, a milk lotion, a powder, an ointment, a spray, a cleanser or a conceal stick. In addition, the composition according to the present disclosure may be used in the form of a foam or an aerosol composition further containing a compressed propellant. These compositions may be prepared by methods commonly employed in the related art.

The cosmetic composition may additionally contain other ingredients that may provide a synergic effect to the main effect, within a range where they do not negatively affect the main effect. The ingredients may be selected by those skilled in the art without difficulty in consideration of the formulation of the cosmetic composition or the purpose of use. For example, the cosmetic composition may further contain a skin absorption promoter in order to increase the effect of the cosmetic composition. In addition, the cosmetic composition of the present disclosure may further contain one or more substance selected from a group consisting of a water-soluble vitamin, an oil-soluble vitamin, a polypeptide, a polysaccharide, a sphingolipid and a seaweed extract.

Moreover, the cosmetic composition of the present disclosure may further contain other ingredients commonly added to a cosmetic composition, as needed, in addition to the essential ingredients. Examples may include an oil, a fat, a moisturizer, an emollient, a surfactant, an organic or inorganic pigment, an organic powder, a UV absorbent, an antiseptic, a disinfectant, an antioxidant, a plant extract, a pH control agent, an alcohol, a colorant, a perfume, a blood circulation promoter, a cooling agent, an antiperspirant, purified water, etc. The additional ingredients that may be contained in the cosmetic composition of the present disclosure are not limited to those described above and they may be added in amounts not negatively affecting the purpose and effect of the present disclosure.

The formulation of the cosmetic composition is not particularly limited and may be selected adequately depending on purposes. For example, it may be formulated into one or more formulation selected from a group consisting of a skin softener (a skin lotion and a milk lotion), a nourishing lotion, an essence, a nourishing cream, a massage cream, a powder, a lipstick, a makeup base, a foundation, a patch, a spray, a pack, a gel, essence, an eye cream, an eye essence, a cleansing cream, a cleansing foam, a cleansing water, a cleanser, a body lotion, a body cream, a body oil and a body essence, although not being limited thereto.

The present disclosure may provide a pharmaceutical composition containing the catechin-free tea water, which is a pharmaceutical composition for recovering skin barrier function or moisturizing skin.

Specifically, the pharmaceutical composition according to the present disclosure may be prepared into a solid, semi-solid or liquid formulation for oral or parenteral administration by adding a commonly used inorganic or organic carrier. The pharmaceutical composition of the present disclosure may be easily formulated according to common methods and a surfactant, an excipient, a colorant, a spice, a stabilizer, an antiseptic, a preservative, a wetting agent, an emulsification promoter, a suspending agent, a salt and/or buffer for control of osmotic pressure or other commonly used adjuvants may be used adequately.

Examples of the formulation for oral administration may include a tablet, a pill, a granule, a soft or hard capsule, a powder, a fine granule, a dust, a liquid, an emulsion, a syrup, a pellet, etc. These formulations may further contain, in addition to the active ingredient, a diluent (e.g., lactose, dextrose, sucrose, mannitol, sorbitol, cellulose or glycine), a lubricant (e.g., silica, talc, stearic acid or its magnesium or calcium salt or polyethylene glycol) or a binder (e.g., magnesium aluminum silicate, starch paste, gelatin, tragacanth, methyl cellulose, sodium carboxymethyl cellulose or polyvinylpyrrolidone). As occasion demands, they may further contain pharmaceutical additives such as a disintegrant such as starch, agar, alginic acid or its sodium salt, an absorbent, a colorant, a flavor, a sweetener, etc. The tablet may be prepared by a common mixing, granulation or coating method. Examples of the formulation for parenteral administration may include a formulation for external application to skin, an injection, a drip, a lotion, an ointment, a gel, a cream, a suspension, an emulsion, a suppository, a patch or a spray, although not being limited thereto.

The pharmaceutical composition according to the present disclosure may be administered orally or parenterally, e.g., rectally, topically, transdermally, intravenously, intramuscularly, intraperitoneally subcutaneously, etc. The administration dosage of the active ingredient will vary depending on the age, sex and body weight of a subject to be treated, the particular disease or pathological condition to be treated, the severity of the disease or pathological condition, the route of administration and the discretion of a diagnoser. The determination of the administration dosage considering these factors is within the level of those skilled in the art.

In an exemplary embodiment, the present disclosure may provide a food composition for recovering skin barrier function or moisturizing skin, which contains the catechin-free tea water. The formulation of the food composition is not particularly limited. It may be in the form of a solid or a drink.

Hereinafter, the present disclosure will be described in detail through examples, comparative examples and test examples. However, the following examples, comparative examples and test examples are for illustrative purposes only and the scope of the present disclosure is not limited by the examples, comparative examples and test examples.

Example 1

Preparation of Catechin-Free Tea Water

As an exemplary embodiment of the present disclosure, a catechin-free tea water was prepared by the following method.

First, 1 kg of raw green tea leaf (fresh leaf, purchased from Jangwon Co. Ltd.) was steamed at 100° C. for 30 seconds within 1 hour after harvesting in order to inactivate enzymes. The enzyme-inactivated raw tea leaf was delivered under cold storage and 3 kg of a tea juice was obtained by squeezing (compressing) the raw tea leaf.

Then, in order to remove catechin, the tea juice was filtered through diatomaceous earth and then through a cartridge filter having a pore size of 1 μm. After adding activated carbon, the tea juice was filtered again through a cartridge filter having a pore size of 1 μm. After mixing the tea juice with water at a ratio of 1:99, 2 ton of a catechin-free tea water was extracted by performing extraction at room temperature for 2 hours.

Then, a catechin-free tea water (Example 1) was prepared by adding fermandiol and biocitro liquid as source materials of 1,3-propanediol in order to prevent proliferation of microorganisms.

The content of catechin contained in the prepared catechin-free tea water was analyzed by high-performance liquid chromatography (HPLC). Specifically, the measurement was made according to the guide to analytical methods of Health Functional Food Code guide with slight modification in injection and concentration conditions. Separation and quantification were performed by HPLC-PDA. The HPLC analysis condition was as follows.

HPLC: Waters Alliance 2695 LC (Waters, Milford, Mass., USA).

Detector: Waters 2996 photodiode array detector (280 nm).

Column: Thermo Syncronis C18 (250×4.60 mm, 5 μm) or equivalent, similar column.

Flow rate: 1.0 mL/min.

Injection volume: 20 μL.

Column temperature: 40° C.

Chamber temperature: 10° C.

Mobile phase: 0.1% acetic acid in DW (solution A), acetonitrile (solution B).

TABLE 1

| Time | Flow rate (mL/min) | % A | % B | Curve |
| --- | --- | --- | --- | --- |
| 0.0 | 1.0 | 90 | 10 | 6 |
| 10.0 | 1.0 | 90 | 10 | 6 |
| 30.0 | 1.0 | 85 | 15 | 6 |
| 42.0 | 1.0 | 80 | 20 | 6 |
| 44.0 | 1.0 | 5 | 95 | 6 |
| 45.0 | 1.0 | 5 | 95 | 6 |
| 49.0 | 1.0 | 90 | 10 | 6 |
| 50.0 | 1.0 | 90 | 10 | 6 |

In order to determine the catechin concentration in the HPLC-analyzed sample (Example 1), gallocatechin (GC), epigallocatechin (EGC), catechin (C), caffeine (CAF), epicatechin (EC), epigallocatechin gallate (EGCG), gallocatechin gallate (GCG), epicatechin gallate (ECG) and catechin gallate (CG) (Sigma-Aldrich, USA) as catechin standards were dissolved in 20 mL of 50% methanol/DW and analyzed by HPLC after diluting to different concentrations. This procedure was repeated independently 3 times and the result was averaged. A standard curve as shown in FIG. 2 was obtained.

Then, the ingredients contained in the catechin-free tea water of Example 1 according to the present disclosure were analyzed by conducting HPLC independently 2 times. The HPLC data were averaged and shown in FIG. 3. Finally, the standard curve (FIG. 2) and the analysis result for Example 1 (FIG. 3) were displayed on one graph (FIG. 4).

Figure 2:
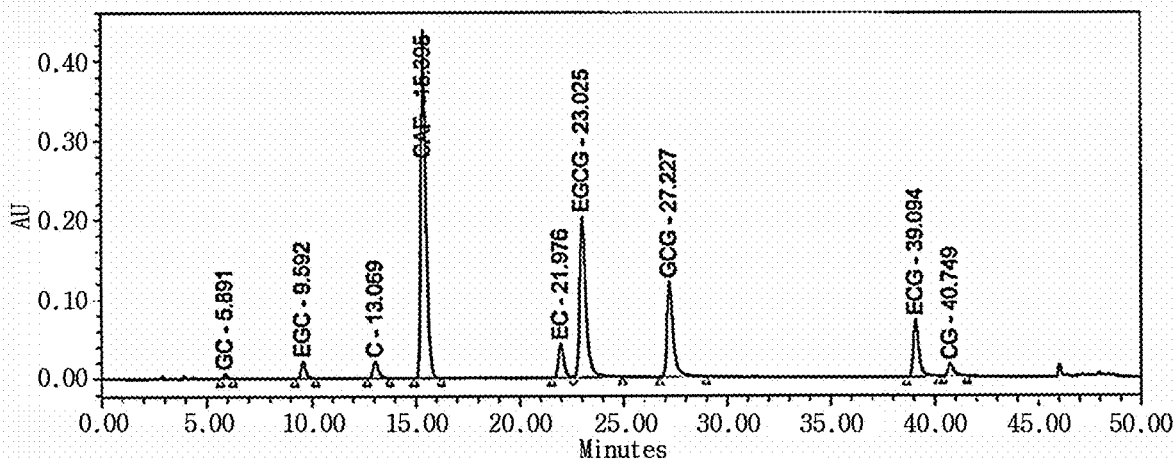
FIG. 2 shows HPLC analysis data (standard curve) for catechins GC, EGC, C, CAF, EC, EGCG, GCG, ECG and CG standard, for analysis of catechins contained in a catechin-free tea water prepared in Example 1.
Figure 3:
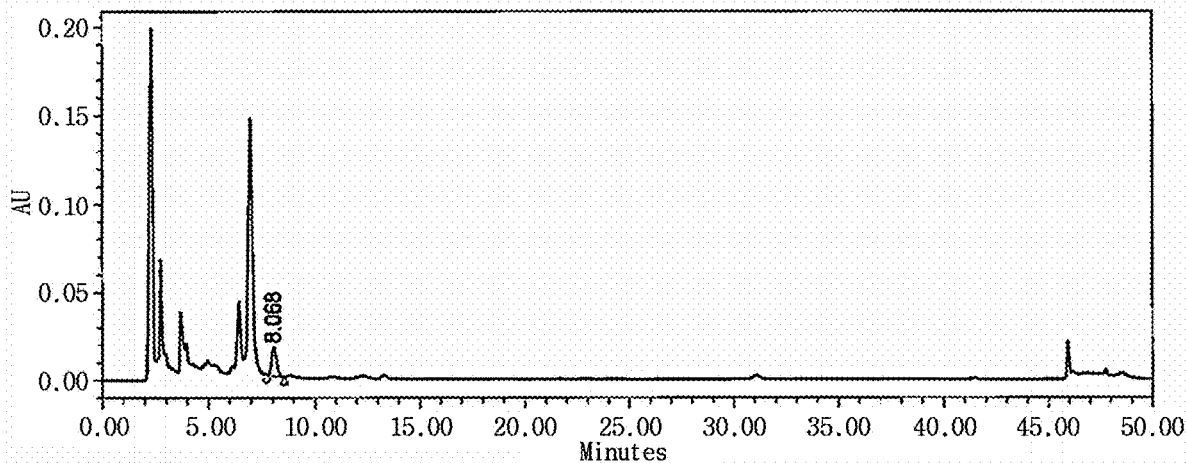
FIG. 3 shows the HPLC analysis result for Example 1, showing that catechin is not contained in the catechin-free tea water of Example 1.
Figure 4:
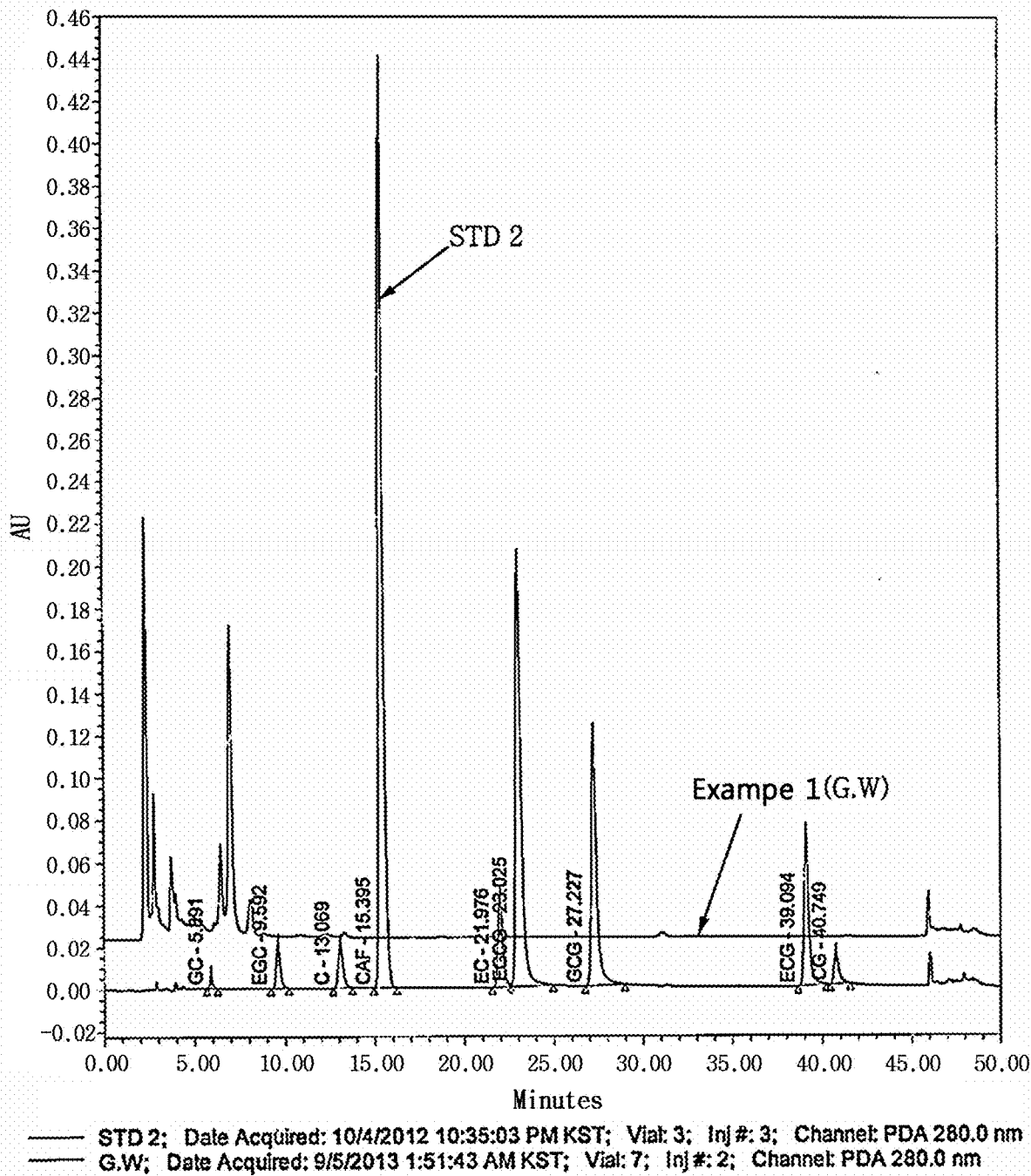
FIG. 4 shows the data for the catechin standard in FIG. 2 and the data for Example 1 in FIG. 3 on one graph.

As can be seen from FIG. 3 and FIG. 4, the peaks found in the catechin standards (FIG. 2) were not observed in the catechin-free tea water of Example 1 according to the present disclosure when compared to HPLC data of the catechin standards of FIG. 2. This indicates that catechin was completely removed in the tea water of Example 1.

Comparative Example 1

Preparation of General Tea Water (Second Flush Tea)

For comparison with the effect of the catechin-free tea water according to the present disclosure, a second flush tea was prepared according to a common method.

First, primarily processed (steaming with steam at 100° C. for 30 seconds→primary drying with hot air at 95° C. for 45 minutes→rolling at room temperature for 20 minutes→secondary drying for 40 minutes→final drying at 90° C.→drying with hot air at 80° C.) green tea was purchased from Jangwon Co. Ltd. Then, after extracting the green tea in cold water for 3 days and then treating with a synthetic antiseptic, a second flush tea (Comparative Example 1) was prepared by filtering through a cartridge filter having a pore size of 1 μm.

Test Example 1

Comparison of Promotion of Filaggrin Gene Expression in Keratinocytes

In order to evaluate the effect of the catechin-free tea water according to an exemplary embodiment of the present disclosure on the differentiation of keratinocytes, the ability of promoting the expression of the filaggrin gene, which is a keratin-binding protein constituting the skin barrier, in keratinocytes was compared with a non-treated group and Comparative Example 1.

First, normal human keratinocytes (NHKs) purchased from Invitrogen (San Diego, Calif., USA) were cultured at 37° C. under a humid atmosphere (95% air and 5% $CO_2$). Then, after treating the normal human keratinocytes with the catechin-free tea water (Example 1) at 50, 100 or 200 ppm (0.005, 0.01 or 0.02%), the second flush tea (Comparative Example 1) at 50, 100, 200 or 500 ppm (0.005, 0.01, 0.02 or 0.05%) or 1.2 mM $Ca^{2+}$ as a positive control for 24 hours, the expression of filaggrin (FLG) was investigated by real-time PCR.

Figure 5:
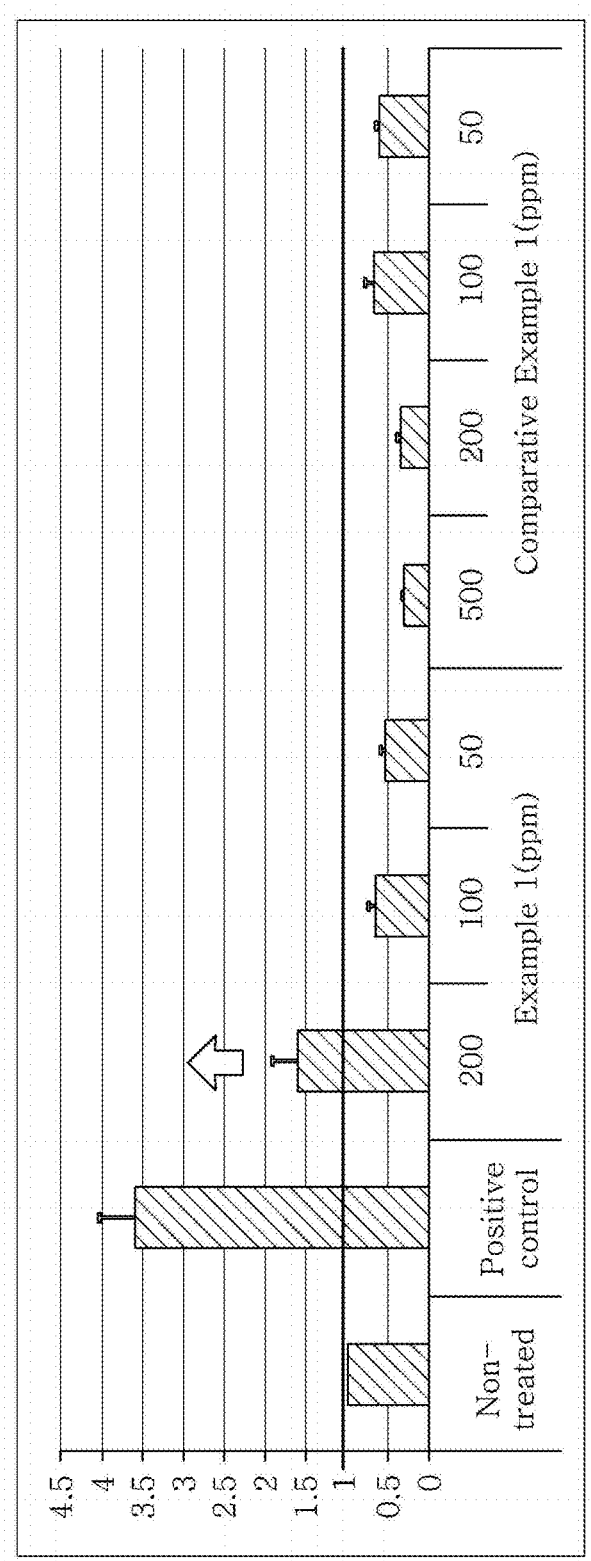
FIG. 5 shows the expression level of the filaggrin gene in keratinocytes treated with nothing (non-treated), a positive control, a catechin-free tea water according to an exemplary embodiment of the present disclosure (Example 1) and a second flush tea (Comparative Example 1).

As seen from FIG. 5, the filaggrin gene was expressed neither for the second flush tea of Comparative Example 1 nor for the catechin-free tea water of Example 1 according to the present disclosure at low concentrations of 50 and 100 ppm (0.005% and 0.01%). At the concentration of 200 ppm (0.02%), the filaggrin expression was increased by 1.5 times or more for the catechin-free tea water of Example 1 according to the present disclosure as compared to the non-treated group, whereas the filaggrin expression decreased for the second flush tea of Comparative Example 1. This indicates that catechin-free tea water can exhibit an effect of recovering or enhancing skin barrier function and moisturizing skin by promoting filaggrin expression, thereby promoting the differentiation of keratinocytes.

Test Example 2

Comparison of Recovery of Skin Barrier Function

The following experiment was conducted to investigate the effect of the catechin-free tea water according to an exemplary embodiment of the present disclosure on the recovery of damaged skin barrier function by skin damage.

First, 22 healthy adult women aged between 20 and 50 years were selected. Their average age was 38.41 years. The recovery of skin barrier function was measured during five visits (visits 1-5). From the second visit (visit 2), the catechin-free tea water of Example 1 was applied on the test area every day at the same hour for a total of 2 weeks. The recovery of transepidermal water loss (TEWL) as a measure of skin hydration and skin barrier function was measured using a vapometer (Delfin VapoMeter SWL4255, Delfin Technologies Ltd, Finland) and the test area was imaged using an image analyzer (Visioscan VC98, Courage-Khazaka Electronic GmbH, Germany). For each measurement and imaging, the area on which the catechin-free tea water of Example 1 was not applied was also measured and imaged as a control.

Specifically, on the first visit, after attaching a patch for damaging skin barrier on the test area of the forearm, the recovery of transepidermal water loss (TEWL) was measured and the test area was imaged (visit 1: day −1). During the second visit on the next day, skin damage was measured and imaged in the same way immediately after removing the patch (visit 2: day 0). Then, the catechin-free tea water of Example 1 was applied on the test area. During the third visit on the next day, skin damage was measured and imaged in the same way (visit 3: day 1). Then, the catechin-free tea water of Example 1 was applied on the test area. Since then, the catechin-free tea water of Example 1 was applied on the test area once every day at the same hour. During the fourth visit a week after the second visit, skin damage was measured and imaged in the same way (visit 4: 1 week). Finally, during the fifth visit two weeks after the second visit, skin damage was measured and imaged in the same way (visit 5: 2 weeks).

Figure 6:
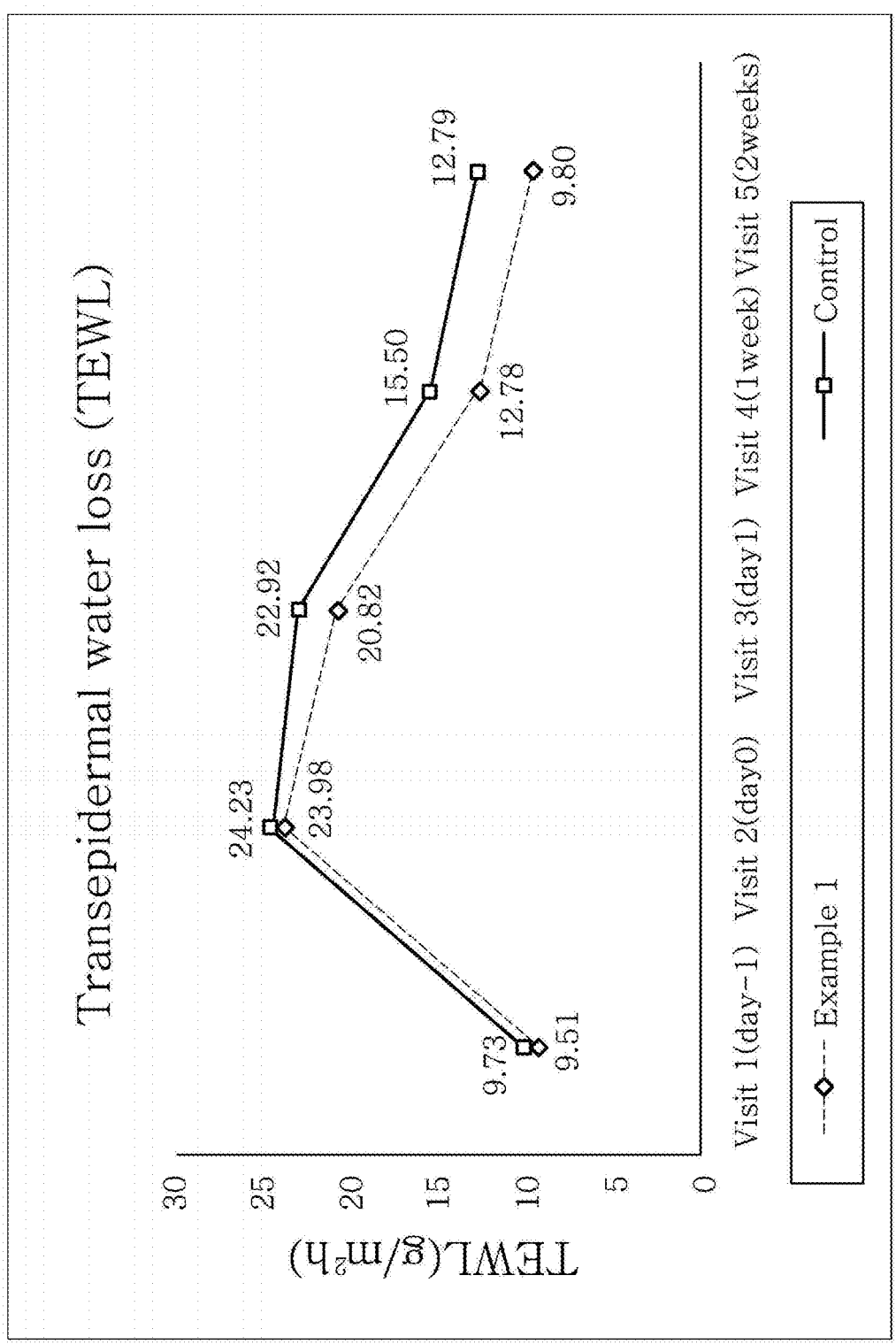
FIG. 6 compares the transepidermal water loss ($g/m^2$ h) of the catechin-free tea water according to an exemplary embodiment of the present disclosure (Example 1) with time with that of a control.

The result of measuring transepidermal water loss (TEWL) with the vapometer during the five visits (visits 1-5) is shown in Table 2 and FIG. 6. And, the change in transepidermal water loss (TEWL change) is shown in FIG. 7.

TABLE 2

| Visit (day) | TEWL change (mean ± SD) | |
|---|---|---|
| | Example 1 | Control |
| Visit 1 (−1, day −1) | 9.51 ± 2.05 | 9.73 ± 1.94 |
| Visit 2 (0, day 0) | 23.98 ± 4.56 | 24.23 ± 4.56 |
| Visit 3 (1, day 1) | 20.82 ± 5.12 | 22.92 ± 5.04 |
| Visit 4 (8, 1 week) | 12.78 ± 1.90 | 15.50 ± 2.24 |
| Visit 5 (15, 2 weeks) | 9.80 ± 1.75 | 12.79 ± 1.88 |

Figure 7:
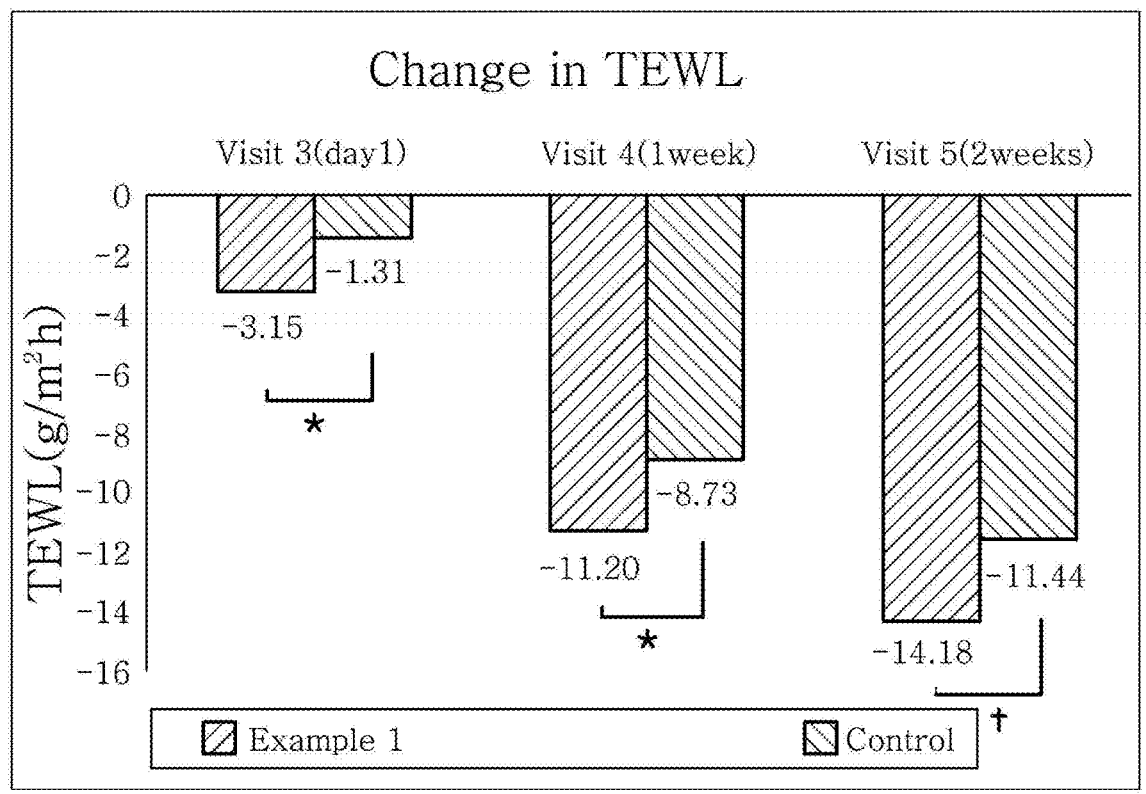
FIG. 7 compares the change in the transepidermal water loss ($g/m^2$ h) of the catechin-free tea water according to an exemplary embodiment of the present disclosure (Example 1) with time with that of a control.

As seen from FIG. 6 and FIG. 7, transepidermal water loss decreased rapidly 1 day (visit 3), 1 week (visit 4) and 2 weeks (visit 5) after the catechin-free tea water of Example 1 according to the present disclosure was applied ($p<0.05$). Specifically, the skin recovery was higher than the control group by 13.72% after 1 day, 45.96% after 1 week and 58.68% after 2 weeks.

Also, a survey (global assessment of efficacy survey) was conducted on the test subjects who used the catechin-free tea water of Example 1. 86%, 82%, 45%, 45% and 91% of the subjects evaluated that the catechin-free tea water of Example 1 was effective respectively in skin hydration, skin texture improvement, applicability, absorption and adhesion and 86% evaluated that the catechin-free tea water of Example 1 had moderate or good fragrance.

Therefore, it was confirmed that the catechin-free tea water according to the present disclosure is superior not only in recovery of skin barrier function but also in skin moisturization, feel in use, and preference such as fragrance.

Test Example 3

Comparison of Skin Moisturization

The following experiment was conducted to investigate the effect of the catechin-free tea water according to an exemplary embodiment of the present disclosure on the continuation of skin moisturization.

First, 21 healthy adult women aged between 20 and 50 years were selected. Their average age was 41.10±4.44 years. The skin moisturization of the test area was measured during three visits. The catechin-free tea water of Example 1 was applied once on the test area of the forearm. The skin moisturization was measured after cleanly washing the test area using a corneometer (CM825, Courage-Khazaka Electronic GmbH, Germany) for 30 minutes under the condition of 20-25° C. and 40-60% humidity. Measurement was made 3 times for the same test area and the result was averaged.

Figure 8:
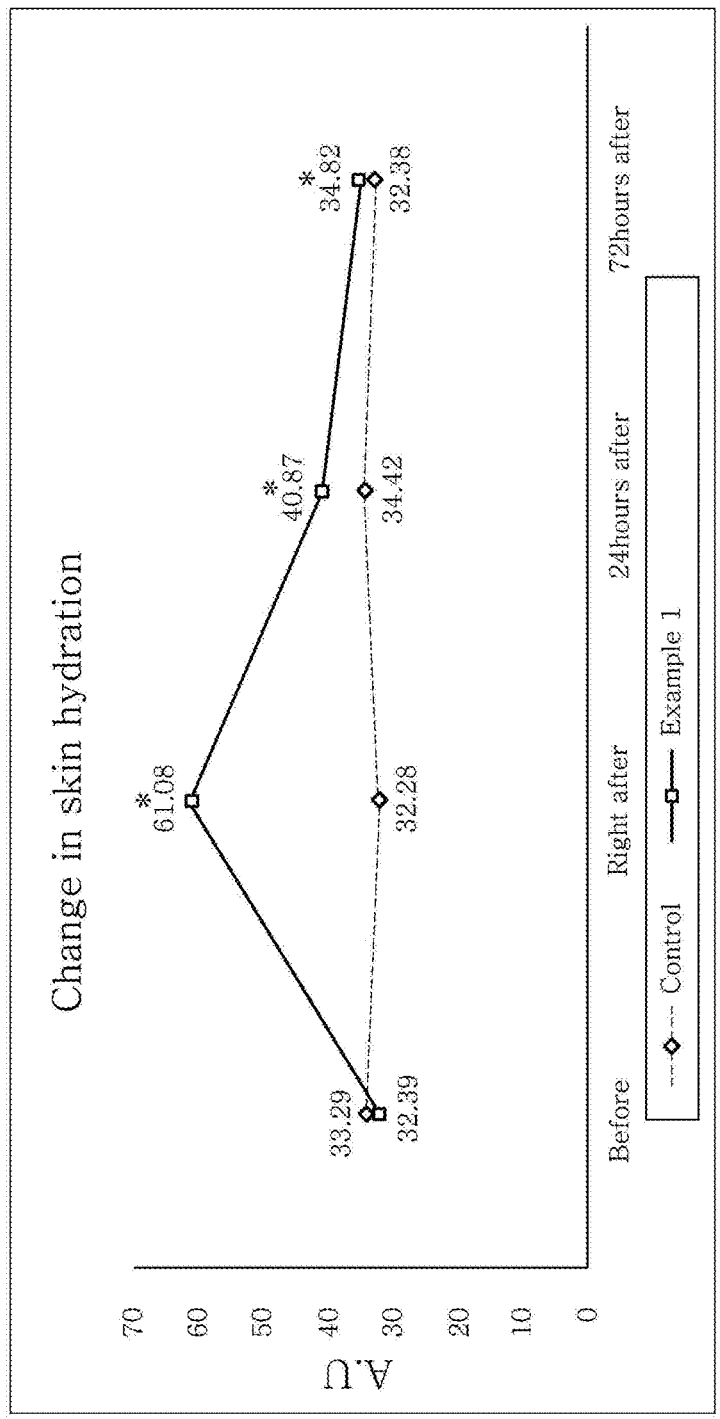
FIG. 8 compares the change in skin hydration (A.U.) of the catechin-free tea water according to an exemplary embodiment of the present disclosure (Example 1) with time with that of a control.

Specifically, on the first visit, skin hydration was measured before and after applying the catechin-free tea water of Example 1. The skin hydration was measured again 24 hours after the application of the catechin-free tea water of Example 1 during the first visit. Finally, the skin hydration was measured again 72 hours after the application of the catechin-free tea water of Example 1 during the first visit. The measurement result is shown in Table 3 and FIG. 8. In FIG. 8, the y-axis indicates skin hydration in arbitrary unit (A.U.).

TABLE 3

| | Skin hydration (mean ± SD) | |
|---|---|---|
| | Control | Example 1 |
| Before application of catechin-free tea water of Example 1 | 33.29 ± 5.57 | 32.39 ± 6.03 |
| Right after application of catechin-free tea water of Example 1 | 32.28 ± 5.73 | 61.08 ± 10.18 |
| 24 hours after application of catechin-free tea water of Example 1 | 34.42 ± 5.97 | 40.87 ± 4.33 |
| 72 hours after application of catechin-free tea water of Example 1 | 32.38 ± 4.67 | 34.82 ± 5.38 |

As seen from Table 3 and FIG. 8, the skin hydration increased significantly right after, 24 hours after and 48 hours after the application of the catechin-free tea water of Example 1 according to the present disclosure and no side effect such as erythema, rash or itchiness was found in any subject.

Also, a survey (global assessment of efficacy survey) was conducted on the test subjects about efficacy and feel in use. 71%, 76%, 66%, 85%, 14% and 57% of the subjects evaluated that the catechin-free tea water of Example 1 was effective respectively in skin hydration, skin texture improvement, absorption, adhesion, fragrance and overall feel in use.

Therefore, it was confirmed that the catechin-free tea water according to the present disclosure retains superior skin moisturizing effect for more than 72 hours without any side effect on skin.

The invention claimed is:

1. A composition for recovering skin barrier function or moisturizing skin in a human, which comprises 0.01 wt. %-100 wt. % of green tea water based on the total weight of the composition, wherein the composition comprises 0.0001 wt. or less of catechins based on the total weight of the composition and wherein the green tea water is a water extract of a tea juice of raw green tea leaves steamed to inactivate enzymes.

2. The composition according to claim 1, wherein the composition is a cosmetic or pharmaceutical composition.

3. The composition according to claim 1, wherein the green tea water promotes differentiation of keratinocytes.

4. The composition according to claim 1, wherein the inactivated enzyme is polyphenol oxidase.

5. The composition according to claim 1, wherein the green tea water is partially obtained by removing catechins in the raw green tea leaf by adsorbing catechins followed by filtering.

6. A method for preparing the catechins free green tea water according to claim 1, which comprises:
   obtaining a green tea juice by steaming raw green tea leaf, thereby inactivating enzymes, and juice-extracting the same; and
   obtaining a catechins free green tea water by removing catechins from the extracted green tea juice to produce the composition of claim 1.

7. The method for preparing the catechins free green tea water according to claim 6, wherein the removing of catechins comprises:
   a deodorization and decoloration step of adsorbing ingredients causing offensive odor generation and discoloration comprising catechins from the extracted green tea juice; and
   a filtration step of filtering the green tea juice that has passed through the deodorization and decoloration step through a filter, thereby removing the adsorbed ingredients causing offensive odor generation and discoloration comprising catechins and residual solids to produce the composition of claim 1.

8. The method for preparing the catechins free green tea water according to claim 7, wherein the deodorization and decoloration step comprises adsorbing the ingredients causing offensive odor generation and discoloration comprising catechins with one or more of diatomaceous earth and activated carbon.

9. The method for preparing the catechins free green tea water according to claim 7, wherein the ingredients causing offensive odor generation and discoloration comprise chlorophyll.

10. The method for preparing the catechins free green tea water according to claim 6, wherein, in the obtaining of the green tea juice, the steaming is performed at 90° C.-110° C. for 0.1 minutes-3 minutes.

11. The method for preparing the catechins free green tea water according to claim 6, wherein the inactivated enzyme is polyphenol oxidase.

12. A method for recovering skin barrier function or moisturizing skin in a human, comprising administering the catechins free green tea water according to claim 1 to a human in need thereof.

* * * * *